US012686710B2

(12) United States Patent
Reitano et al.

(10) Patent No.: US 12,686,710 B2
(45) Date of Patent: Jul. 21, 2026

(54) ANTI-HER2 POLYPEPTIDES DERIVATIVES AS NEW DIAGNOSTIC MOLECULAR PROBES

(71) Applicant: BRACCO IMAGING S.P.A., Milan (IT)

(72) Inventors: Erika Reitano, Banchette (IT); Alessandro Maiocchi, Monza (IT); Luisa Poggi, Turin (IT); Federico Crivellin, Grugliasco (IT); Simon Huet, Nantes (FR); Mathieu Cinier, Nantes (FR); Olivier Kitten, Indre (FR)

(73) Assignee: BRACCO IMAGING S.P.A., Milan (IT)

( * ) Notice: Subject to any disclaimer, the term of this patent is extended or adjusted under 35 U.S.C. 154(b) by 1069 days.

(21) Appl. No.: 17/786,669

(22) PCT Filed: Dec. 16, 2020

(86) PCT No.: PCT/EP2020/086395

§ 371 (c)(1),
(2) Date: Jun. 17, 2022

(87) PCT Pub. No.: WO2021/122726

PCT Pub. Date: Jun. 24, 2021

(65) Prior Publication Data

US 2023/0203129 A1 Jun. 29, 2023

(30) Foreign Application Priority Data

Dec. 18, 2019 (EP) .................................... 19217623

(51) Int. Cl.
*C07K 14/71* (2006.01)
*C07K 1/13* (2006.01)
*G01N 33/533* (2006.01)

(52) U.S. Cl.
CPC ................ *C07K 14/71* (2013.01); *C07K 1/13* (2013.01); *G01N 33/533* (2013.01)

(58) Field of Classification Search
CPC ........ C07K 14/71; C07K 1/13; C07K 14/705; G01N 33/533; A61K 49/0032; A61K 49/0056; A61K 51/088
See application file for complete search history.

(56) References Cited

U.S. PATENT DOCUMENTS 8,389,227 B2 3/2013 Lopez et al.

FOREIGN PATENT DOCUMENTS

| | | | |
|---|---|---|---|
| CN | 102202692 | A | 9/2011 |
| CN | 105693860 | A | 6/2016 |
| WO | 2008068637 | A2 | 6/2008 |
| WO | 2009080810 | A1 | 7/2009 |
| WO | 2012096760 | A1 | 7/2012 |
| WO | 2014140882 | A2 | 9/2014 |
| WO | 2016162505 | A1 | 10/2016 |
| WO | 2017013129 | A1 | 1/2017 |
| WO | 2017161096 | A1 | 9/2017 |
| WO | 2019118721 | A2 | 6/2019 |

OTHER PUBLICATIONS

Bornhorst, J.A. et al., Purification of Proteins Using Polyhistidine Affinity Tags, Methods Enzymol. 326:245-254 (2000).
Goux M. et al., "Nanofitin as a New Molecular-Imaging Agent for the Diagnosis of Epidermal Growth Factor Receptor Over-Expressing Tumors," Bioconjugate Chem. 28:2361-2371 (2017).
Huet S. et al., "Use of the Nanofitin Alternative Scaffold as a GFP-Ready Fusion Tag," PLoS ONE, 10(11): e0142304, (2015).
International Search Report and Written Opinion for PCT/EP2020/086395, mailed Mar. 16, 2021.
McAfee J.G. et al., "Gene Cloning, Expression, and Characterization of the Sac7 Proteins from the Hyperthermophile Sulfolobus acidocaldarius," Biochemistry, 34:10063-10077 (1995).
Mouratou B. et al., "Remodeling a DNA-binding protein as a specific in vivo inhibitor of bacterial secretin PuID," PNAS, 104(46):17983-17988 (2007).
Orlova, A. et al., "Tumor Imaging Using a Picomolar Affinity HER2 Binding Affibody Molecule," Cancer Res. 66(8):4339-4348 (2006).
Slamon D.J. et al., "Studies of the HER-2/neu Proto-oncogene in Human Breast and Ovarian Cancer," Science, 244:707-712 (1989).
Zhang, X et al., "Chapter 1:Antibody mimetics, peptides, and peptidomimetics," In: Tiller, T., Synthetic Antibodies: Methods and Protocols, vol. 1575, pp. 3-13 (2017).

*Primary Examiner* — Erinne R Dabkowski
(74) *Attorney, Agent, or Firm* — VIVICAR Law, PLLC

(57) ABSTRACT

The present invention provides new polypeptide derivatives binding to Human Epidermal Growth Factor Receptor 2 (HER2) and their conjugates thereof, and to their use as a diagnostic agent, particularly for early detection, patient stratification and treatment monitoring of forms of cancer characterized by over-expression of HER2.

20 Claims, 8 Drawing Sheets

Specification includes a Sequence Listing.

a)

b)

a)

b)

SEQUENCE LISTING

<160> NUMBER OF SEQ ID NOS: 5

<210> SEQ ID NO 1
<211> LENGTH: 64
<212> TYPE: PRT
<213> ORGANISM: Sulfolobus acidocaldarius

<400> SEQUENCE: 1

```
Val Lys Val Lys Phe Gly His Met Gly Glu Glu Lys Glu Val Asp Thr
1               5                   10                  15

Ser Lys Ile Tyr Ala Val Asn Arg Ala Gly Lys Phe Val His Phe Ala
            20                  25                  30

Tyr Asp Asp Asn Gly Lys Phe Gly Ser Gly Ser Val Pro Glu Lys Asp
        35                  40                  45

Ala Pro Lys Glu Leu Leu Asp Met Leu Ala Arg Ala Glu Arg Glu Lys
    50                  55                  60
```

<210> SEQ ID NO 2
<211> LENGTH: 77
<212> TYPE: PRT
<213> ORGANISM: Artificial Sequence
<220> FEATURE:
<223> OTHER INFORMATION: Engineered HER2 binding polypeptide

<400> SEQUENCE: 2

```
Met Arg Gly Ser His His His His His His Gly Ser Val Lys Val Lys
1               5                   10                  15

Phe Gly His Met Gly Glu Glu Lys Glu Val Asp Thr Ser Lys Ile Tyr
            20                  25                  30

Ala Val Asn Arg Ala Gly Lys Phe Val His Phe Ala Tyr Asp Asp Asn
        35                  40                  45

Gly Lys Phe Gly Ser Gly Ser Val Pro Glu Lys Asp Ala Pro Lys Glu
    50                  55                  60

Leu Leu Asp Met Leu Ala Arg Ala Glu Arg Glu Lys Cys
65                  70                  75
```

<210> SEQ ID NO 3
<211> LENGTH: 12
<212> TYPE: PRT
<213> ORGANISM: Artificial Sequence
<220> FEATURE:
<223> OTHER INFORMATION: Synthetic 6xHis Tag derivative

<400> SEQUENCE: 3

```
Met Arg Gly Ser His His His His His His Gly Ser
1               5                   10
```

<210> SEQ ID NO 4
<211> LENGTH: 76
<212> TYPE: PRT
<213> ORGANISM: Artificial Sequence
<220> FEATURE:
<223> OTHER INFORMATION: Engineered HER2 binding polypeptide

<400> SEQUENCE: 4

```
Met Arg Gly Ser His His His His His His Gly Ser Val Lys Val Lys
1               5                   10                  15

Phe Gly His Met Gly Glu Glu Lys Glu Val Asp Thr Ser Lys Ile Tyr
            20                  25                  30

Ala Val Asn Arg Ala Gly Lys Phe Val His Phe Ala Tyr Asp Asp Asn
        35                  40                  45
```

-continued

```
Gly Lys Phe Gly Ser Gly Ser Val Pro Glu Lys Asp Ala Pro Lys Glu
    50                  55                  60

Leu Leu Asp Met Leu Ala Arg Ala Glu Arg Glu Lys
65                  70                  75


<210> SEQ ID NO 5
<211> LENGTH: 434
<212> TYPE: PRT
<213> ORGANISM: Artificial Sequence
<220> FEATURE:
<223> OTHER INFORMATION: Engineered HER2 binding polypeptide

<400> SEQUENCE: 5

Met Arg Gly Ser His His His His His His Gly Ser Val Lys Val Lys
1               5                   10                  15

Phe Gly His Met Gly Glu Glu Lys Glu Val Asp Thr Ser Lys Ile Tyr
            20                  25                  30

Ala Val Asn Arg Ala Gly Lys Phe Val His Phe Ala Tyr Asp Asp Asn
        35                  40                  45

Gly Lys Phe Gly Ser Gly Ser Val Pro Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Ala Gly Ser Ala Ala Gly Ser Gly Glu Phe Gly Gly Ser Leu Ala Ala
                85                  90                  95

Leu Thr Ala His Gln Ala Cys His Leu Pro Leu Glu Thr Phe Thr Arg
            100                 105                 110

His Arg Gln Pro Arg Gly Trp Glu Gln Leu Glu Gln Cys Gly Tyr Pro
        115                 120                 125

Val Gln Arg Leu Val Ala Leu Tyr Leu Ala Ala Arg Leu Ser Trp Asn
    130                 135                 140

Gln Val Asp Gln Val Ile Arg Asn Ala Leu Ala Ser Pro Gly Ser Gly
145                 150                 155                 160

Gly Asp Leu Gly Glu Ala Ile Arg Glu Gln Pro Glu Gln Ala Arg Leu
                165                 170                 175

Ala Leu Thr Leu Ala Ala Ala Glu Ser Glu Arg Phe Val Arg Gln Gly
            180                 185                 190

Thr Gly Asn Asp Glu Ala Gly Ala Ala Ser Gly Pro Ala Asp Ser Gly
        195                 200                 205

Asp Ala Leu Leu Glu Arg Asn Tyr Pro Thr Gly Ala Glu Phe Leu Gly
    210                 215                 220

Asp Gly Gly Asp Val Ser Phe Ser Thr Arg Gly Thr Gln Asn Trp Thr
225                 230                 235                 240

Val Glu Arg Leu Leu Gln Ala His Arg Gln Leu Glu Glu Arg Gly Tyr
                245                 250                 255

Val Phe Val Gly Tyr His Gly Thr Phe Leu Glu Ala Ala Gln Ser Ile
            260                 265                 270

Val Phe Gly Gly Val Arg Ala Arg Ser Gln Asp Leu Asp Ala Ile Trp
        275                 280                 285

Arg Gly Phe Tyr Ile Ala Gly Asp Pro Ala Leu Ala Tyr Gly Tyr Ala
    290                 295                 300

Gln Asp Gln Glu Pro Asp Ala Arg Gly Arg Ile Arg Asn Gly Ala Leu
305                 310                 315                 320

Leu Arg Val Tyr Val Pro Arg Ser Ser Leu Pro Gly Phe Tyr Arg Thr
                325                 330                 335
```

-continued

```
Gly Leu Thr Leu Ala Ala Pro Glu Ala Ala Gly Glu Val Glu Arg Leu
            340                 345                 350

Ile Gly His Pro Leu Pro Leu Arg Leu Asp Ala Ile Thr Gly Pro Glu
        355                 360                 365

Glu Glu Gly Gly Arg Leu Glu Thr Ile Leu Gly Trp Pro Leu Ala Glu
    370                 375                 380

Arg Thr Val Val Ile Pro Ser Ala Ile Pro Thr Asp Pro Arg Asn Val
385                 390                 395                 400

Gly Gly Asp Leu Asp Pro Ser Ser Ile Pro Asp Lys Glu Gln Ala Ile
                405                 410                 415

Ser Ala Leu Pro Asp Tyr Ala Ser Gln Pro Gly Lys Pro Pro Lys Asp
            420                 425                 430

Glu Leu
```

ANTI-HER2 POLYPEPTIDES DERIVATIVES AS NEW DIAGNOSTIC MOLECULAR PROBES

CROSS-REFERENCE TO RELATED APPLICATIONS

This application is the national stage application of corresponding international application number PCT/EP2020/086395, filed Dec. 16, 2020, which claims priority to and the benefit of European application no. 19217623.8, filed Dec. 18, 2019, which is hereby incorporated by reference in its entirety.

The present invention relates to new polypeptide derivatives which bind to Human Epidermal Growth Factor Receptor 2 (HER2) and their conjugates thereof, and to their use as diagnostic agents, particularly for early detection, patient stratification and treatment monitoring of forms of cancer characterized by over-expression of HER2.

BACKGROUND

In recent years biomarkers discovery is emerging as a dynamic and powerful approach for its potential in identifying the earliest events for a pathological state, both in diagnostic and therapeutic fields. It is also becoming extremely challenging to develop probes able to recognize a target involved in a molecular pathway of a disease state. These probes have to be able to improve the diagnostic procedures for better application of current therapeutic regimens, improving the therapy efficacy and reducing patients overtreatments.

The proto-oncogene HER2 or HER2/neu (Human Epidermal Growth Factor Receptor 2) encodes the production of a cell surface receptor, known as HER2 protein or receptor, a member of ErbB family of tyrosine kinase receptors involved in transmission of signals controlling normal cell growth and differentiation. Due to errors in the DNA replication system in tumor cells, HER2 gene can be amplified leading to an over-expression of the HER2 protein on the cells surface. In particular, over-expression of the HER2 receptor occurs in 25-30% of human breast primary carcinomas[1] and has been described in correlation with many other HER2 positive tumors, including for instance head&neck cancer, ovarian cancer, lung cancer, bladder cancer and tumors of the gastrointestinal tract.

For these reasons, HER2 represents an important molecular target for many oncological therapies and diagnostic methods. Among the approaches to inhibit HER2 protein on tumor cell surfaces, some therapies using humanized variants of monoclonal antibodies, e.g. trastuzumab and pertuzumab, have become commercially available in recent years for the treatment of HER2-positive tumors; however, despite the clinical success, their use is associated with some toxic effects and undesired side-effects on healthy tissues which are a reason of concern.

In general, many antibodies are characterized by slow and inefficient tumor penetration, long biodistribution time and slow clearance from the blood, and, for diagnostic applications, require the use of long-lived radioisotopes and imaging at late time points, thus exposing patients to a high radiation burden. Additionally, monoclonal antibodies may be immunogenic, thus precluding repeated administration for routine diagnostic procedures.

Therefore, there is still a high need to a continued provision of new molecules able to interact with HER2 forms.

These problems could be circumvented for instance by the use of small molecules.

Recently, small binding polypeptides (4 to 20 kDa), such as for instance affibodies, fibronectins and DARPins, have been described and are attracting interest as potential alternatives to antibodies for use in non-invasive imaging methods. Generally, such peptides have demonstrated to be biocompatible and poorly immunogenic in vivo, highly selective and able to bind and recognize specific targets, and present an affinity constant ($K_d$) in the nanomolar range, lower than the antibodies, the latters generally having a $K_d$ in the milli/micromolar range. Also, small polypeptides penetrate tissues faster and more efficiently because of their significantly lower molecular weight and can distinguish extracellular or intracellular domains of proteins, which cannot be differentiated by antibodies.

Moreover, unlike antibodies and other large macromolecules ($M_w$~150 kDa), small molecules clear rapidly from circulation and thus reach at early time-points after administration a tumor/blood ratio suitable for imaging. This in turn allows physicians to obtain diagnostic information much more quickly than with antibody-based imaging agents.

In particular, the development of new small imaging probes binding HER2 receptor can be of great value providing specific imaging agents for patient stratification, for predicting or monitoring the response to specific anti-cancer therapies and even in the image-guided surgery of the tumors by means of optical imaging, magnetic resonance imaging, nuclear imaging, computed tomography imaging, ultrasound and multimodality imaging techniques.

In particular, among the class of antibody-mimetic molecules, affitins are compounds consisting of small, single-chain affinity proteins (7 kDa, generally 66 amino acids) which are being studied for their high tissue penetration potential. Known examples of such peptides are Nanofitins® (Affilogic S.A.S., France). These polypeptides are derived from the hyperstable DNA-binding protein Sac7d of the thermophilic archaeon *Sulfolobus acidocaldarius*, from which they retain most of the advantageous biophysical features, such as resistance to temperature (up to 90° C.) and pH (0-13). In particular, high-affinity affitins are engineered with several rounds of ribosome display by the full randomization of 10-14 amino acid residues in the DNA-binding site of Sac7d and can be tuned to have high affinity towards specific targets expressed on the surface of cancer cells, while conserving the original stability features of being thermophilic and acidophilic[2,3].

Moreover, besides being extremely stable and robust, affitin polypeptides have better pharmacokinetic profiles for imaging with respect to antibodies and can easily produced in large quantities employing recombinant bacterial technologies.

For instance, Goux M. et al., *Bioconjugated Chem.* 2017, 28, 2361-2371[4] discloses the use of the anti-EGFR Nanofitin B10 as imaging agent, in particular as a target PET radiotracer, when radiolabeled with $^{18}$F-FBEM. However, no specific sequences of affitins binding the target HER2 have been described yet.

Among the known antibody-mimetic polypeptides, several sequences of affibodies binding to HER2 have been investigated, such as those described in WO2009/080810[5] in the name of Affibody AB and in Orlova A. et al., *Cancer Res.* 2006, 66(8), 4339-4348[6].

An example of application of such HER2-binding polypeptides as imaging agents after conjugation with a radionuclide and a chelator is reported in WO2012/0967607 in the name of GE Healthcare Ltd and Affibody AB.

WO2017/161096[8], in the name of Tarveda Therapeutics Inc., discloses nano- and micro-particles comprising generic conjugates with a targeting moiety, such as for instance a Nanofitin, a linker and an active agent, even though without reporting any specific example of such conjugates.

Therefore, despite the efforts, there is still the need to identify and develop HER2 binding agents as described above, characterized by a high and specific affinity for the target, to be used as diagnostic agents of HER2-positive tumors, in particular for monitoring the treatments of HER2-positive tumors.

SUMMARY

The present invention relates to new polypeptides sequences, characterized by the affitins structure, specifically targeting HER2 receptor with high affinity.

In particular the invention relates to HER2-binding polypeptides comprising the amino acid sequence:

(SEQ ID NO: 1)
VKVKFGHMGEEKEVDTSKIYAVNRAGKFVHFAYDDNGKFGSGSVPEKDA
PKELLDMLARAEREK.

Considering the overexpression of HER2 protein as a marker of pathological states, being involved in breast cancer and in many other types of tumor, the HER2-binding affitins of the invention may be useful, once labelled with an imaging moiety, for an early cancer diagnosis and staging in the perspective of more effective therapeutic treatments and/or of reducing patients overtreatments.

To this purpose, they can be efficiently conjugated to labelling moieties, allowing an easy recognition and evaluation during in vitro and/or in vivo analyses. Such conjugates or complexes are also object of the present invention.

The affitins of the invention were found endowed with suitable properties for their use in diagnostic tools, such as a nanomolar affinity for the target HER2, absence of binding to albumins, low predicted immunogenicity, good internalization in HER2-positive cells and a good expression yield. In particular, the affitins of the invention and their conjugates are able to specifically recognize the target at the site where it is physiologically present, i.e. on the cell surface where HER2 is expressed, thus allowing possible in vivo applications thereof.

Moreover, it has been found that the affitins of the invention are able to recognize the target HER2 at a specific epitope distinct from that recognized by the monoclonal antibodies trastuzumab and pertuzumab, currently used in clinical treatment of HER2-positive tumors, thus allowing for instance the use of the affitins of the invention as agents to test for changes in HER2 receptor expression in response to trastuzumab and/or pertuzumab therapy.

DESCRIPTION OF THE DRAWINGS

The features of the invention can be better understood with reference to the following detailed description and the accompanying figures, wherein.

BRIEF DESCRIPTION OF THE SEQUENCE LISTING

Figure 1:
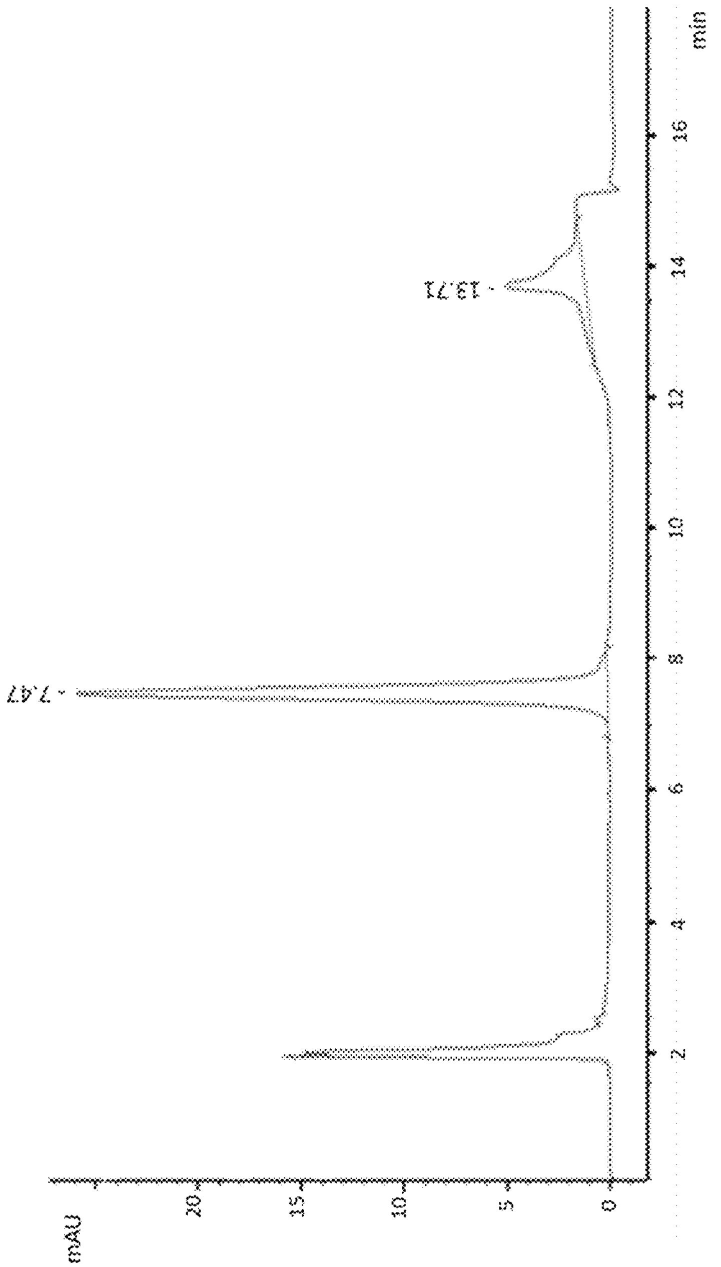
FIG. 1 represents an RP-HPLC chromatogram of Aff04 polypeptide, showing the presence of a dimeric form.

SEQ ID NO: 1 sets out the 64 aac sequence of the affitin of the invention named Aff03:

VKVKFGHMGEEKEVDTSKIYAVNRAGKFVHFAYDDNGKFGSGSVPEKDA
PKELLDMLARAEREK;

SEQ ID NO: 2 sets out the 77 aac sequence corresponding to a derivatized variant of SEQ ID NO: 1, engineered with a Cys at the C-terminus and a hexahistidine tag at the N-terminus, named affitin Aff04:

MRGSHHHHHHGSVKVKFGHMGEEKEVDTSKIYAVNRAGKFVHFAYDDNG
KFGSGSVPEKDAPKELLDMLARAEREKC;

SEQ ID NO: 3 identifies the $His_6$-tag derivative linked to the N-terminus of the affitin Aff04 and Aff04-0:

MRGSHHHHHHGS;

SEQ ID NO: 4 is an engineered polypeptide corresponding to Aff04 (SEQ ID NO: 2) without the C-terminal cysteine and is named Aff04-0:

MRGSHHHHHHGSVKVKFGHMGEEKEVDTSKIYAVNRAGKFVHFAYDDNG
KFGSGSVPEKDAPKELLDMLARAEREK;

SEQ ID NO: 5 identifies the engineered polypeptide formed by fusion of the sequence Aff04-0 (SEQ ID NO: 4) with a truncated portion of *Pseudomonas* exotoxin A (Pe38):

MRGSHHHHHHGSVKVKFGHMGEEKEVDTSKIYAVNRAGKFVHFAYDDNG
KFGSGSVPEKDAPKELLDMLARAEREKKLGSAGSAAGSGEFGGSLAALT
AHQACHLPLETFTRHRQPRGWEQLEQCGYPVQRLVALYLAARLSWNQVD
QVIRNALASPGSGGDLGEAIREQPEQARLALTLAAAESERFVRQGTGND
EAGAASGPADSGDALLERNYPTGAEFLGDGGDVSFSTRGTQNWTVERLL
QAHRQLEERGYVFVGYHGTFLEAAQSIVFGGVRARSQDLDAIWRGFYIA

-continued

GDPALAYGYAQDQEPDARGRIRNGALLRVYVPRSSLPGFYRTGLTLAAP

EAAGEVERLIGHPLPLRLDAITGPEEEGGRLETILGWPLAERTVVIPSA

IPTDPRNVGGDLDPSSIPDKEQAISALPDYASQPGKPPKDEL.

DETAILED DESCRIPTION

It is an object of the present invention to provide new agents with affinity for Human Epidermal Growth Factor Receptor 2 (HER2), in particular a polypeptide that is characterized by specific binding to HER2 and its derivatives and conjugates thereof.

Thus, in a first aspect, the invention provides a polypeptide that specifically binds to HER2 comprising the amino acid sequence VKVKFGHMGEEKEVDTSKIYAVNRAGKFVHFAYDDNGKFGSGSVPEKDAPKELLD MLARAEREK (SEQ ID NO: 1). Preferably, such sequence has a length of up to 100 amino acids. More preferably, it has a length of up to 80 amino acids.

In a preferred specific embodiment, the invention provides the polypeptide consisting of the amino acid sequence as set out in SEQ ID NO: 1.

Different modifications of, and/or addition to, the polypeptides above defined may be performed, without departing from the scope of the present invention, including for instance addition of further amino acids to the sequence, derivatization with any linker or spacer, or conjugation with specific labels or imaging moieties, as described in more detail below.

For instance, the invention also encompasses polypeptides in which the HER2 binding polypeptide described above bears additional amino acid residues added at one or both terminal positions, provided that they not alter the biological function of said peptides. These additional amino acid residues may play a role in the binding of HER2 by the polypeptide, but may equally well serve other purposes, related for example to the production, purification, stabilization, coupling and/or detection of the polypeptide. Preferably, such additional amino acid residues may comprise one or more amino acid residues added for purposes of chemical coupling. A preferred embodiment relates to the addition at the very first or very last position in the polypeptide chain, i.e. at the N or C terminus, of at least one amino acid containing a thiol group, such as cysteine or homocysteine, or containing in the side chain a primary amino group, such as lysine, or a carboxylic acid group, such as glutamic acid or aspartic acid.

In another embodiment, such residue to be used for chemical coupling may also be introduced by replacement of another amino acid on the surface of the protein domain, preferably on a portion of the surface that is not involved in target binding.

In some embodiments, said residue suitable for the coupling can also be represented by a synthetic or unnatural amino acid or an amino acid mimetic that function similarly to the natural occurring amino acids. Non-limiting examples are selected from $\beta^2$- or $\beta^3$-amino acids; γ-amino acids; substituted glycine or alanine, such as p-acetophenylalanine or p-azidophenylalanine; 6-amino hexanoic acid and other derivatives known in the art, which are useful to modulate the coupling strategy or to confer stability to the conjugate.

The additional amino acid residues may also comprise a "tag" useful for the purification, isolation or detection of the polypeptide, such as for instance a hexahistidyl tag, or a "myc" tag or a "FLAG" tag for interaction with antibodies specific to the tag, or other alternatives well known to the skilled person, which can be alone or coupled to a binding target.

Accordingly, in another preferred embodiment the invention provides a HER2 binding polypeptide comprising the amino acid sequence MRGSHHHHHHGSVKVKFGHMGEEKEVDTSKIYAVNRAGKFVHFAYDDNGKFGSGS VPEKDAPKELLDMLARAEREKC (SEQ ID NO: 2), corresponding to the peptide of SEQ ID NO: 1 modified by addition of a Cys at the C-terminus and of the $His_6$-tag of amino acid sequence MRGSHHHHHHGS (SEQ ID NO: 3) at the N-terminus.

In a preferred embodiment the invention provides the HER2 binding polypeptide consisting of the amino acid sequence as set out in SEQ ID NO: 2.

In another preferred embodiment the invention provides a HER2 binding polypeptide comprising the amino acid sequence MRGSHHHHHHGSVKVKFGHMGEEKEVDTSKIYAVNRAGKFVHFAYDDNGKFGSGS VPEKDAPKELLDMLARAEREK (SEQ ID NO: 4), corresponding to the peptide of SEQ ID NO: 1 modified by addition of the $His_6$-tag of amino acid sequence MRGSHHHHHHGS (SEQ ID NO: 3) at the N-terminus.

In another embodiment the invention provides the HER2 binding polypeptide consisting of the amino acid sequence as set out in SEQ ID NO: 4.

In particular, the additional hexahistidine-tag at the N-terminus of the peptide is useful for purification of the protein by Ni-NTA column, following known procedures, as described for instance in Bornhorst J. A. et al, *Methods Enzymol.* 2000, 326, 245-254[9].

The invention also encompasses multimers of the polypeptide, such as a dimer, comprising sequence SEQ ID NO: 1. For instance, in one embodiment the invention provides for a homodimer molecule including two polypeptides comprising amino acid sequence SEQ ID NO: 1 or a heterodimer molecule including a polypeptide comprising amino acid sequence SEQ ID NO: 1 and a different polypeptide with high binding affinity for HER2 or for other target molecules, in order to create multispecific reagents that may be used in several biotechnological applications.

The linked polypeptide "units" in such multimers according to the invention may be connected by covalent coupling using known organic chemistry methods, or expressed as one or more fusion polypeptides in a system for recombinant expression of polypeptides, or joined in any other fashion, either directly or via a linker, for example an amino acid linker.

All the above defined polypeptides can be considered as a suitable alternative to antibodies against HER2 in several applications. An aspect of the invention thus relates to a HER2 binding polypeptide as described above which is conjugated to a compound or labeled to form a reporter moiety amenable to be used in diagnosis or imaging of a cancer disease caused by and/or associated with an overexpression of HER2.

A "reporter moiety" refers to a molecule that can be directly or indirectly detected by an imaging technique, wherein the HER2 binding polypeptides of the invention are linked to at least one detectable label or material (e.g. a dye whose optical properties can be measured; a contrast agent comprising a magnetic particle; or a gas containing vesicle). A reporter moiety is undirectly detectable for instance when it becomes detectable only through interaction with an environment or a further material modifying its detectability.

Suitable imaging techniques for detection of such reporter moieties include for instance magnetic resonance, positron-emission tomography (PET), computed tomography (CT), ultrasounds (US), photoacoustic imaging (PAI), near-infrared fluorescence (NIRF) and single photon emission computed tomography (SPECT) or techniques correlated with optical imaging (OI).

In particular, PET imaging techniques also include immunoPET, wherein a specific biomarker information on a disease is obtained by directly targeting the receptor of interest, for instance with antibodies or antibody-mimetic molecules.

For imaging applications, the polypeptides of the invention are linked to a label generally selected from: a fluorophore moiety capable of generating a fluorescent signal, such as fluorescein, FITC, Alexa dyes, Cyanine dyes, DyLight dyes, IRDye dyes or VivoTag dyes; an optical moiety, including agents that may be used to produce contrast or signal using optical imaging; a magnetic or paramagnetic moiety, including a chelating agent for magnetic resonance which is able to form stable complexes with paramagnetic metal ions, including for instance Gd(III), Mn(II), Cr(III), Cu(II), Fe(III), Pr(III), Nd(III), Sm(III), Tb(III), Yb(III), Dy(III), Ho(III) and Er(III); a radiolabeled isotope, including for instance $^{18}F$, $^{124}I$, $^{11}C$, $^{64}Cu$, $^{68}Ga$, $^{89}Zr$, $^{44}Sc$ and $^{99m}Tc$ and other radioisotopes of indium, gallium, yttrium, bismuth, radioactinides and radiolanthanides; an affinity label, such as biotin; an X-ray responsive moiety that may be used to produce contrast or signal using X-ray imaging, such as iodinated organic molecules or chelates of heavy metal ions; an ultrasound responsive moiety or assembly for contrast enhanced ultrasound imaging, preferably in the form of a gas-filled microbubble; a photoacoustic responsive imaging moiety, including photoacoustic imaging-compatible agents; and nanoparticle-based moieties.

Preferably, in case of labeling with radionuclides, such complexation is performed with the use of chelators or multidentate ligands, forming chelates in particular with the radiometals. Non-limiting examples of such chelators are 1,4,7,10-tetraazacyclododecane-1,4,7,10-tetraacetic acid (DOTA); 2,2',2''-(1,4,7-triazacyclononane-1,4,7-triyl)triacetic acid (NOTA); 2-[bis[2-[bis(carboxymethyl)amino]ethyl]amino]acetic acid (DTPA); ethylenediaminetetraacetic acid (EDTA), 10-(2-hydroxypropyl)-1,4,7-tetraazacyclododecane-1,4,7-triacetic acid (HP-DO3A); 1,4-bis(carboxymethyl)-6-[bis(carboxymethyl)]amino-6-methylperhydro-1,4-diazepine (AAZTA) and derivatives thereof.

Accordingly, in a preferred embodiment the invention encompasses a radiolabeled polypeptide consisting of a chelate of a HER2 binding polypeptide described above and a radionuclide, such as a radioactive metal. More preferably, the radioactive metal is $^{68}Ga$, $^{44}Sc$ or $^{99m}Tc$.

In another preferred embodiment, the polypeptides of the invention are conjugated with a fluorophore moiety selected from the cyanine dyes, such as for instance IRDye800CW, IRDye650, IRDye680, Cy3, Cy5, Cy5.5, Cy7, ZW800-1, AlexaFluor 750 AlexaFluor 790, and analogues and derivatives thereof.

Moreover, the polypeptide and the label may be linked using a tag system, including biotin/avidin, biotin/streptavidin and biotin/NeutrAvidin.

Accordingly, in a further preferred aspect, the invention provides for polypeptides as defined above which are linked to an affinity label, such as biotin.

The coupling between the targeting polypeptide of the invention and the label or imaging moiety can be performed through methods described herein in the examples or other methods well known to the skilled person. For instance they may be linked either covalently or noncovalently, optionally by interposition of a suitable linker or spacer, useful for labeling.

Generally, such linkers or spacers may comprise amino acids or nucleic acids sequences or reactive moieties including for instance an aminoxy group, an azido group, an alkyne group, a thiol group or a maleimido group, either alone or in combination.

Such linkers preferably comprise two functional moieties, one providing rapid and efficient labeling and another enabling rapid and efficient coupling to the polypeptides of the invention, for instance through an amine group or preferably through the thiol group of the cysteine. For example a maleimide group reacts with thiol groups to form a stable thioether bond. Preferably, the final complex is formed by first reacting the label with the linker, and subsequently with the thiol group of the polypeptide.

The polypeptides of the invention, suitably conjugated with a label to form a reporter moiety, can be used in the diagnosis and staging of HER2-related states, disorders, dysfunctions, conditions or diseases and for monitoring of the treatment response in such states, particularly for targeting in the clinical setting of cancer diseases characterized by an overexpression of HER2 protein. Exemplary applications include the diagnosis of a cancer disease correlated with the expression of HER2, such as for instance breast cancer, head&neck cancer, ovarian cancer, lung cancer, bladder cancer and tumors of the gastrointestinal tract.

Accordingly, in a further aspect the invention provides a polypeptide conjugate as defined above for use in diagnosis or visualization of a cancer disease caused by and/or associated with an overexpression of HER2, i.e. in a process of identifying or determining the nature and cause of a HER2-correlated disease through evaluation of patient history, examination and review of laboratory data. In particular, such polypeptide conjugate may be used for imaging of a body tissue or organ system overexpressing HER2. More preferably, it can be used to determine HER2 expression before and after a treatment, which can be accomplished by obtaining images before and after the treatment, and to determine the extent or anatomical content of HER2 expression, e.g. for surgical purposes or for patients stratification.

In yet another aspect, the invention provides the use of a polypeptide conjugate as described above in the preparation of an imaging agent for detecting a cancer tissue or organ characterized by overexpression of HER2.

In a further aspect, the invention provides a composition comprising a polypeptide or polypeptide conjugate as herein defined and one or more suitable pharmaceutically acceptable carriers, excipients, diluents and/or additives. The ingredients of the composition can be varied depending on the intended use, whether for diagnostic or imaging applications. Such composition can also comprise one or more adjuvants selected from preservatives, wetting agents, emulsifying agents and dispersing agents.

The composition can further contain one or more different imaging agents.

In one embodiment, the invention provides the composition as said above for use in imaging of a target tissue bearing HER2, wherein the composition comprises a polypeptide of the invention conjugated or labeled with an imaging moiety as above defined. The composition can be e.g. also in the form of a liposome or nanoparticles and can be suitable for different types of administration. Preferably, said imaging is performed with an imaging technique selected from magnetic resonance, positron-emission tomography (PET), computed tomography (CT), ultrasounds (US), photoacoustic imaging (PAI), near-infrared fluorescence (NIRF) and single photon emission computed tomography (SPECT), or correlated with optical imaging (OI).

In one embodiment the composition is suitable for parenteral administration, preferably for intravenous or subcutaneous administration, for instance in the form of sterile aqueous solutions or dispersions or powders for the preparation of sterile injectable solutions, dispersions or emulsion formulations. In another embodiment the above composition may be administered topically or by inhalation.

Said compositions are provided for use with an imaging technique for visualizing HER2 expressing tumors, such as breast cancer.

In another aspect, the invention provides for a kit that contains at least one polypeptide of the invention, preferably labeled or conjugated with an imaging moiety, in one or more containers and the instructions for use.

The invention also provides for a method for an in vivo imaging of at least a portion of a mammalian subject, preferably a human, having a cancer characterized by over-expression of HER2, such method comprising the steps:

administering a composition as described above to the subject;

optionally monitoring the delivery of the composition to the subject;

imaging the subject with a diagnostic device; and optionally diagnosing the subject with a HER-2-associated disease condition.

The polypeptides of the invention can be obtained by recombinant expression, i.e. by sequence cloning in an expression plasmid, which can be expressed for instance in *Escherichia coli*, and purification by affinity chromatography, for instance following the procedure described in Huet S. et al, *PLoS ONE* 2015, 10 (11): e0142304[10].

For instance, precultures can be grown overnight at 37° C. in medium with glucose and antibiotics. Precultures can be diluted in medium with glucose and antibiotics, and grown at 37° C. to mid-log phase. Then, protein expression can be induced by addition of Isopropyl β-D-1-thiogalactopyranoside and the culture shaken at 30° C. overnight. Bacteria can be pelleted by centrifugation, then resuspended in a lysis buffer. Cell lysis can be performed at room temperature for 1 h and the suspension centrifuged to remove cell debris. Histag-proteins can then be purified from supernatants by immobilized metal ion affinity chromatography (IMAC), using Nickel resin and an elution buffer containing 250 mM Imidazole.

Another aspect of the present invention relates to a nucleic acid molecule which encodes a polypeptide as described above.

In a further embodiment the invention relates to an expression vector comprising the nucleic acid molecule said above and optionally other nucleic acid elements that enable production of the polypeptide according to the invention through expression of the nucleic acid molecule.

Moreover, the invention relates to a host cell (e.g. a eukaryotic, prokaryotic or plant cell) comprising said expression vector.

The above aspects represent recombinant techniques for the production of a polypeptide of the invention which are well known to the skilled person.

Alternatively, the polypeptides of the invention may also be produced by other known means, including chemical synthesis, for instance with standard solid phase synthesis techniques, or expression in different hosts, such as for instance plants and transgenic animals.

The invention will now be illustrated in detail through the description of examples performed in accordance therewith.

Experimental Section

The following examples are provided for illustration only and should not be construed as limiting the invention.

Equipment

The sequences and conjugates thereof of the present invention, as prepared according to the following examples, were characterized by UV/VIS (optical density), SE-HPLC, RP-HPLC and MALDI-TOF MS analytical data, by use of one of the following methods:

SE-HPLC: The Size Exclusion HPLC analysis was carried out at 30° C. at a flow rate of 1 ml/min using a Sepax Zenix SEC-80 4.6×300 mm column (injection volume: 10 μL). The instrument was equipped with a UV/VIS detector at 280/780 nm. The mobile phase was 150 mM phosphate buffer, pH 7.0.

RP-HPLC: Unless stated otherwise, HPLC analyses were performed at 40° C. at a flow rate of 1.2 ml/min using a Jupiter Proteo (Phenomenex) 4.6×250 mm column (injection volume: 10 μL). The instrument was equipped with a UV/VIS detector at 280/780 nm. Mobile phase A was 0.1% TFA in water and mobile phase B was 0.1% TFA in acetonitrile. The gradient is reported below:

| Gradient: | | |
|---|---|---|
| Min | % A | % B |
| 0 | 72 | 28 |
| 2 | 72 | 28 |
| 8 | 65 | 35 |
| 9 | 10 | 90 |
| 11 | 10 | 90 |
| 12 | 72 | 28 |
| 17 | 72 | 28 |

MALDI-TOF MS: Mass spectra were acquired by a MALDI-TOF Ultraflex II mass spectrometer (Bruker Daltonics). Samples were pre-treated by loading onto a 10 μL Pipette tip C18 ZipTip to remove salts and eluted in 10 μL volume. Mass spectra were acquired over m/z range from 600 to 20,000 after sample purification, using samples with final concentration of 100 μM.

Flow cytometry analysis (FACS) was performed with a BD Accuri™ C6 flow cytometer (BD Biosciences)

Affinity experiments were performed by Biolayer Interferometry (BLI) assay, using an Octet System and Protein A biosensors (ForteBio). Recombinant human protein hHER2 was purchased from R&D Systems (Minneapolis, US).

In vivo imaging experiments were performed using the IVIS Spectrum In Vivo Imaging System (Perkin Elmer Inc.), equipped with 10 narrow band excitation filters (30 nm bandwidth) and 18 narrow band emission filters (20 nm bandwidth) spanning 430-850 nm.

Purification of the Aff04-AAZTA conjugate was performed by preparative HPLC on a Waters AutoPurification system, equipped with 3100 Mass Detector, 600 Quaternary Pump Gradient Module, 2767 Sample Manager and 2487 UV/Visible Detector. The purification was performed employing an Atlantis prepD® $C_{18}$OBD 5 μm (19×100 mm) column. Eluent A: 0.1% TFA in $H_2O$; eluent B: 0.1% TFA in $CH_3CN$. Gradient profile: isocratic at 10% of B for 10 min, linear gradient from 10% to 100% of B in 1 min, isocratic at 100% of B for 2 min. Flow rate: 20 mL/min.

The purity of the products was monitored by analytical HPLC employing a Waters 2695 Alliance Separation Module equipped with a Waters 2998 Photodiode Array Detector and using:

(for AAZTA derivative) a Waters Atlantis DC18 5 μm (4.6×150 mm) column. Gradient profile: 0 min 10% B, 5 min 10% B, 15 min 65% B, 20 min 100% B, 25 min 100% B. Flow rate: 1 mL/min; λ: 210 nm: or (for Aff04-AAZTA conjugate) a Waters Xterra RP8 5 μm, 4.6×150 mm column. Gradient profile: 0 min 25% B, 5 min 25% B, 11 min 33% B, 15 min 33% B, 17 min 80% B, 18 min 95% B, 20 min 95% B.

List of Abbreviations

HER2 Human Epidermal Growth Factor Receptor 2
kDa kiloDalton
HSA Human serum albumin
MSA Mouse serum albumin
BSA Bovine serum albumin
ELISA Enzyme-linked immunosorbent assay
BLI Biolayer interferometry
$K_d$ Dissociation equilibrium constant
aac Amino acid
RT Room temperature
Pe38 Truncated portion of *Pseudomonas* exotoxin A
TCEP Tris(2-carboxyethyl) phosphine
UV/VIS Ultraviolet/visible spectrophotometry
SE-HPLC Size exclusion high performance liquid chromatography
RP-HPLC Reversed-phase High Performance Liquid Chromatography
DTT Dithiothreitol
MALDI-TOF Matrix-assisted laser desorption/ionization-time-of-light mass spectrometry
PBS Phosphate-buffered saline
TBS-T Tris-buffered saline-Tween 20
TMB Tetramethylbenzidine
TCEP Tris(2-carboxyethyl) phosphine
HRP Horseradish peroxidase
DIPEA N,N-Diisopropylethylamine
HATU 1-[Bis(dimethylamino)methylene]-1H-1,2,3-triazolo[4,5-b]pyridinium 3-oxid hexafluorophosphate
TFA Trifluoroacetic acid
TIS Triisopropylsilane The abbreviations for individual amino acids residues are conventional: for example, Cys or C is cysteine, Asp or D is aspartic acid, Gly or G is glycine, Arg or R is arginine. The amino acids, as herein referred to, should be understood to be of the L-isomer configuration unless otherwise noted.

Example 1: Preparation of the Affitins According to the Invention

To selectively target HER2 receptor, a library of affitins has been enriched against the target by several consecutive rounds of screening (up to 6 rounds). The enrichment of anti-HER2 afftins has been followed after any selection round by ELISA assay monitoring, also controlling the condition of negligible binding to human (HSA), murine (MSA) and bovine (BSA) serum albumin. At the end of the selection process, the affitin named Aff03 (SEQ ID NO: 1) has been found endowed with nanomolar affinity to HER2, absence of binding to albumin and low in silico immunogenity.

The polypeptide Aff04 was obtained by sequencing the selected clone identified during the screening step. The sequence, including the N-terminal $His_6$-tag (MRGSHHHHHHGS, SEQ ID NO: 3) and the C-terminal Cys-tag, was subcloned in *Escherichia coli* DH5α LacIq strain, following the procedure described in Huet S. et al, *PLoS ONE* 2015, 10(11): e0142304[10]. Briefly, DNA amplicon encoding SEQ ID NO: 1 was subcloned in a plasmid derived from pQE-30 (Qiagen) by Gibson assembly to encode SEQ ID NO: 2, and the ligation mixture was transformed into *Escherichia coli* DH5α LacIq strains (Invitrogen). Clones were isolated and selected on 2×YT medium plates containing 100 μg/ml ampicillin and 25 μg/ml kanamycin. The plasmid construction was confirmed by Sanger sequencing. Precultures from transformed *Escherichia coli* DH5α LacIq were grown overnight at 37° C. in 2×YT medium with 1% glucose, 100 μg/ml ampicillin and 25 μg/ml kanamycin. Precultures were diluted 1:20 in 2×YT medium with 0.1% glucose, 100 μg/ml ampicillin and 25 μg/ml kanamycin, and grown at 37° C. to mid-log phase (OD600=0.8-1.0). Then, protein expression was induced by addition of Isopropyl β-D-1-thiogalactopyranoside to the final concentration of 0.5 mM and the culture shaken at 30° C. overnight. Bacteria were pelleted by 45 min centrifugation at 3220 g. Cell pellets were resuspended in a pH 7.4 lysis buffer composed of 1× BugBuster Protein Extraction Reagent, 5 g/ml DNaseI, 20 mM Tris, 500 mM NaCl, and 25 mM Imidazole. Cell lysis occurred at room temperature for 1 h and the suspension was centrifuged at 3220 g for 45 min to remove cell debris. Histag-proteins were then purified from supernatants by immobilized metal ion affinity chromatography (IMAC), using His60 Nickel Superflow resin (Clontech) and a pH 7.4 elution buffer composed of 20 mM Tris, 500 mM NaCl, and 250 mM Imidazole. Additional endotoxin removal step was carried over for samples engaged in cell-based assay. First, samples were buffer-exchanged by dialysis against PBS (10 mM phosphate, 2.7 mM KCl and 137 mM NaCl, pH 7.4; Sigma-Aldrich). Then, samples were filtered on a Sartobind STIC PA anion exchanger (Sartorius). Finally, samples were dialyzed against PBS, filtered on Minisart hydrophilic membranes with 0.2 μm pore size (Sartorius), then stored in sterile conditions.

Such derivatized affitin was named Aff04 (SEQ ID NO: 2).

Example 2: Determination of Cells Internalization of the Affitin Aff03

The cells internalization of Aff03 was evaluated using a dedicated cell-based assay. Briefly, Aff03 was tagged with SEQ ID NO: 3 (i.e. forming sequence Aff04-0) and then fused to a truncated portion of *Pseudomonas* exotoxin A, wherein the cell internalization domain of the toxin is removed, thus forming a final peptide with the sequence as set out in SEQ ID NO: 5. Such truncated form (Pe38) needs to be internalized by means of the Aff03 to keep its cytotoxic activity.

To test internalization, then, the viability of the breast adenocarcinoma cell line SK-BR-3 (overexpressing HER2 receptor) and of the breast cancer cell line MCF-7 (low expressing HER2 receptor) was measured at different nanofitin concentrations. A dose-dependent cytotoxic induction was observed on SK-BR-3 cells, while, on the contrary, no significant alterations were observed on MCF-7 cells.

Cell death induction demonstrated an effective transport of Pe38 through HER2 receptor due to Aff03 triggering internalization.

Example 3: Coupling of Affitin Aff04 to IRDye800CW-Maleimide

IRDye800CW-maleimide was purchased (Li-Cor Inc., USA) in order to conjugate an activated form of this fluorophore IRDye800CW to the reactive cysteine-tag at the C-terminus of affitin Aff04 (SEQ ID NO: 2).

Since the terminal free cysteine is highly reactive, it also leeds to the formation of a dimeric form of the protein in stock solutions. A disulphide bridge between the Cys terminal residues of two monomers is indeed formed in the presence of oxygen. Therefore, a reduction step on the Aff04 stock solution prior to conjugation was performed. The Aff04 stock solution was reduced in phosphate buffer (0.02 M phosphate, 0.054 M KCl, 0.274 M NaCl, pH 7.4) by incubation with a mild reducing agent (TCEP). In details, 50 μL of 0.5 M of TCEP were added to 5 mg of affitin Aff04 and incubated for 1-16 h (preferably 1-2 h) at room temperature. The obtained monomeric protein was purified from the excess of reducing agent with a Desalting Column (e.g. Zeba Desalting Spin Column, Thermo Scientific).

Purified Aff04 was then incubated with 5 mg of IRDye800CW-maleimide (dissolved in 500 μL of DMSO) for 1-3 h, preferably 2 h, at room temperature in dark condition to avoid bleaching. At the end of reaction, the conjugate named IRDye800CW-Aff04 was purified on a desalting column, as described above.

The fractions containing the conjugate IRDye800CW-Aff04 were collected and characterized by measuring their optical density from 230 to 830 nm by UV/VIS spectrophotometry, and by SE-HPLC (see FIG. 1) and RP-HPLC. IRDye800CW-Aff04 resulted at concentration of 1.71 mg/mL (Molar Extinction Coefficient: 12051.52 $M^{-1}$ $cm^{-1}$).

RP-HPLC analysis was also performed in order to check the reduction of the dimeric protein. The chromatograms of the dimer and of Aff04 conjugated to IRDye800CW showed that the reduction of disulfide bridges was efficiently performed prior to conjugation.

The validation of the fluorescent probe was tested on cell surface by flow cytometry.

Example 4: Coupling of Affitin Aff04 to AAZTA Chelator

The chelator 1,4-bis(carboxymethyl)-6-[bis(carboxymethyl)]amino-6-methylperhydro-1,4-diazepine (AAZTA) was prepared according to the following reaction scheme 1:

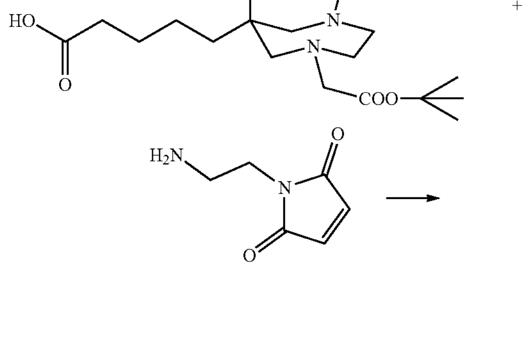

-continued

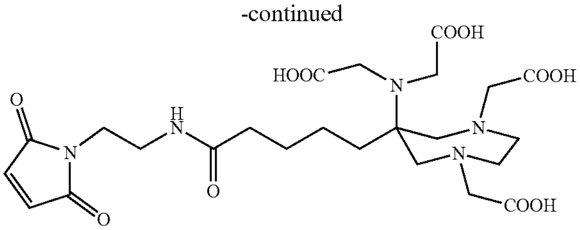

Briefly, in a 10 mL round bottom flask, 50 mg of (tBu) 4-AAZTA-C4-COOH (0.0744 mmol) were dissolved in 5 mL of methylene chloride and DIPEA (3 eq., 0.223 mmol, 39 μL) and HATU (0.9 eq., 0.0670 mmol, 25.5 mg) were added to the reaction solution. After 10 minutes, 1.1 eq. of 1-(2-aminoethyl) maleimide hydrochloride (0.0819 mmol, 14.5 mg) was added to the obtained solution. After 1 h, the solution was washed with water (3×2 mL) and brine (1×1 mL), anhydrified on $Na_2SO_4$, filtered and evaporated in vacuo. The residue was dissolved in TFA/TIS 95:5 (3 mL) and left to stir 5 h at room temperature. The crude product was precipitated in cold diethyl ether (100 mL) and purified by preparative HPLC on a Waters AutoPurification system. AAZTA-N-ethylmaleimide was isolated as a homogenous peak with retention time of about 4.3 min. All fractions containing the final product were collected, evaporated and lyophilized to give AAZTA-N-ethylmaleimide as a white solid. The purity of the product was monitored by analytical HPLC. RT: 7.065 min.

HPLC Purity: 99%, p: 11.84 mg, overall yield: 28%.

ESI-MS (m/z): calcd: for $C_{24}H_{35}N_5O_{11}$ (M/Z)+570.57 found: 570.33.

Conjugation Step:

To the Aff04 affitin solution, under argon atmosphere, 5 eq of TCEP were added. After 30 minutes an HPLC analysis confirmed the complete reduction of the disulfide bond. 10 eq of AAZTA-N-ethylmaleimide were added to the solution and the reaction was stirred for 45 minutes at room temperature. An HPLC analysis confirmed the complete conversion to the desired product. The solution was purified twice on a Zeba Spin Desalting Column 7K MWCO in order to separate all AAZTA-N-ethylmaleimide from the Aff04-AAZTA solution. The collected solution was quantified by UV Spectrophotometry at 280 nm (ε 2980 $cm^{-1}M^{-1}$). The product was characterized by LC/MS on a Waters 2695 Alliance Separation Module.

HPLC purity 98%

Calc. MW: 9243.22; (M(H+)12/12): 771.28; Exper. MW (M(H+)12/12): 771.25

Example 5: Analytical Characterization

Analytical characterization of the non-conjugated affitin Aff04 was performed by MALDI-TOF mass spectrometry with the conditions described above. After pre-treatment with 10 μL Pipette tips C18 ZipTip for removal of salts, the samples (10 μL) were treated with 2 μL of DTT (20 mM in PBS) for reduction of the sulfured bridges between two C-terminal Cys and the reaction was incubated for 15 minutes at 50° C., then chilled on ice. The obtained monomer was then alkylated in order to avoid further dimerization. To this purpose, 2 μL of iodacetamide (40 mM in PBS) was added, and the reaction incubated for 15 minutes at room temperature. Then, samples were again loaded onto a 10 μL Pipette tip C18 ZipTip for purification.

Figure 2:
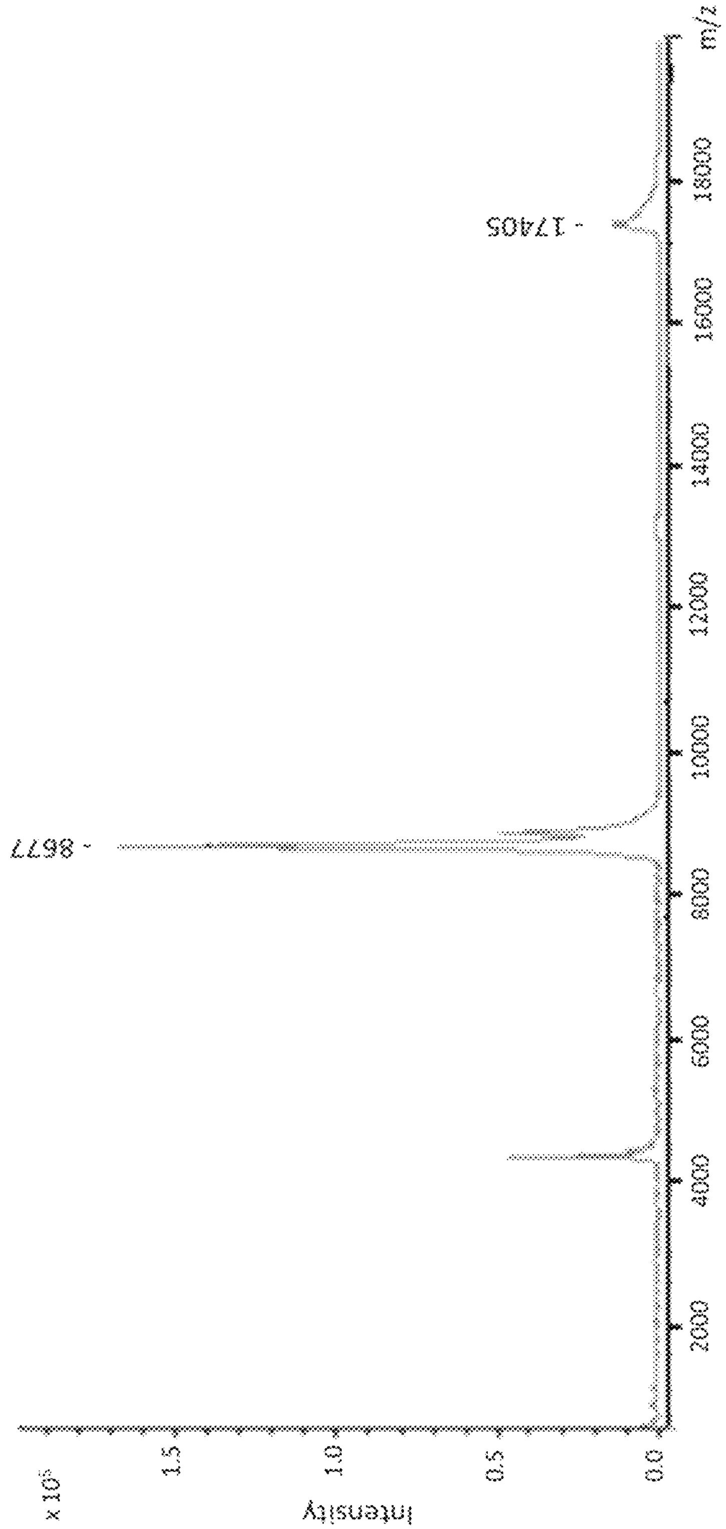
FIG. 2 represents a MALDI-TOF mass spectrum of Aff04 polypeptide (acquisition range 600-20,000 m/z) after reduction of disulphide bridges and alkylation.

The MS spectra acquired over m/z range 600 to 20,000 on the unconjugated polypeptide showed the presence of two major peaks at m/z 8677 and 17405, the first peak being related to the monomeric peptide and the second to the dimeric peptide, formed by creation of the sulfured bridges. After reduction and alkylation of the affitin Aff04, the contribution of the first peak increased while the second peak diminished, as shown in FIG. 2.

Example 6: In Vitro Affinity Assay of the Unlabeled Affitin Aff04-0 to HER2 Receptor The affinity of the polypeptides of the invention for the target HER2 was measured by Biolayer interferometry assay. To this purpose, the protein A biosensors (ForteBio) were coated with human HER2 (hHER2) recombinant protein. After a brief wash with PBS, the coated sensor was assayed versus the affitin Aff04-0 at different concentrations (i.e. 10000, 500, 250, 125, 62.5, 31.3, 15.6 and 0 nM).

A curve fitting analysis was then performed in order to determine the dissociation equilibrium constant. The sensorgrams were analyzed using the Octet Data Analysis software 8.2 (ForteBio) with a 1:1 binding fit model to determine the dissociation equilibrium constant ($K_d$) and the related association and dissociation rate constants ($k_{on}$ and $k_{off}$) with $R^2$ value assessing the fitting quality.

The resulting kinetic profiles showed a $K_d$ associated to Aff04-0 affitin in the nanomolar range, in particular a $K_d$ of $2.2±0.1×10^{-8}$ M, as summarized in the following Table 1.

TABLE 1

| Dissociation equilibrium constants of the hHER2-Aff04-0 complex | |
|---|---|
| | Unlabeled Aff04-0 affitin |
| $K_d$ (M) | $2.2 \pm 0.1 \times 10^{-8}$M |
| $k_{on}$ ($M^{-1}s^{-1}$) | $1.7 \pm 0.1 \times 10^{6}M^{-1}s^{-1}$ |
| $k_{off}$ ($s^{-1}$) | $3.8 \pm 0.1 \times 10^{-2}$ $s^{-1}$ |
| $R^2$ | 0.9732 |

Example 7: In Vitro Affinity Assay of the IRDye800CW-Aff04 Conjugate to HER2 Receptor The affinity of the IRDye800CW-Aff04 conjugate to the target HER2 was measured by Biolayer interferometry assay. To this purpose, the protein A biosensors (ForteBio) were coated with human HER2 (hHER2) recombinant protein. After a brief wash with PBS, the coated sensor was assayed versus the IRDye800CW-Aff04 conjugate at different concentrations (i.e. 10000, 1000, 100, 10, 1, 0.1 ng/ml).

A steady state analysis was performed in order to determine the dissociation equilibrium constant. The sensorgrams were analyzed using the Octet Data Analysis software 8.2 (ForteBio) with a 1:1 binding fit model to determine the dissociation equilibrium constant ($K_d$). The resulting kinetic profiles showed a $K_d$ associated to IRDye800CW-Aff04 conjugate in the nanomolar range, as reported in Table 2.

These data show that the coupling of the fluorophore to the C-terminal cysteine affitin Aff04 did not significantly changed the $K_d$ compared to the unlabeled Aff04-0.

TABLE 2

| Dissociation equilibrium constants of the complex IRDye800CW-Aff04 conjugate/hHER2 | |
|---|---|
| | IRDye800CW-Aff04 conjugate |
| $K_d$ (M) | $1.1 \pm 0.1 \times 10^{-8}$M |

Example 8: In Vitro Affinity on Cells of the Affitin IRDye800CW-Aff04 Conjugate

In order to assess the binding specificity of the conjugate IRDye800CW-Aff04, flow cytometry analysis (FACS) was performed with two different types of human cancer cell lines, in particular the breast adenocarcinoma cell line SK-BR-3, overexpressing HER2 receptor (HER2+), and the epidermoid carcinoma cell line A431, not expressing HER2 receptor (HER2-). The whole procedure was carried out keeping the cells on ice (at 4° C.) in order to evaluate the ability of the conjugate IRDye800CW-Aff04 to bind the exposure receptors. Briefly, 200,000 SK-BR3 (HER2+) and A431 (HER2−) cells per sample were distributed in 1.5 mL eppendorf tubes in 50 μL of FACS buffer (PBS/0.5% BSA/0.1% $NaN_3$). The conjugate IRDye800CW-Aff04 was incubated onto cells at growing concentrations, 1 hour 30 minutes on ice. The concentrations tested were 17, 13, 8.5, 4.25, 2.12, 1.06, 0.53, 0.26 and 0.065 μM.

After 3 washes in FACS buffer by centrifugation 450 RCF 5 min 4° C., the flow cytometry analysis was carried out with 640 nm (excitation wavelength) and Em 670LP (long pass filter) for detecting the IRDye800CW fluorophore. The recorded fluorescence values were analyzed with non-linear regression fitting by GraphPad Prism 7 software.

Figure 3:
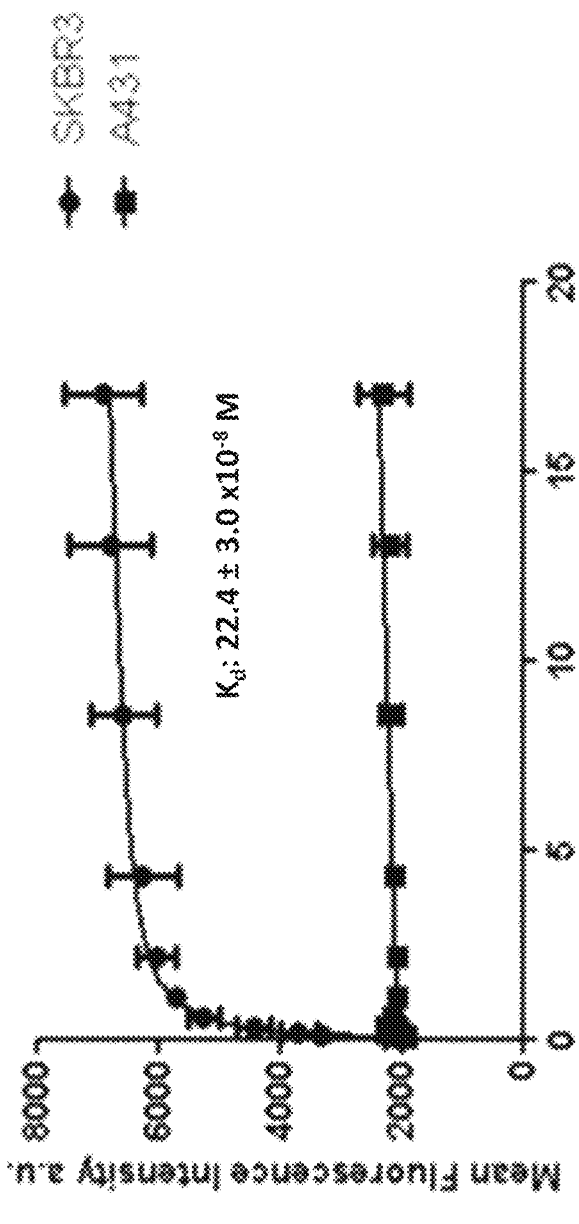
FIG. 3 reports an affinity determination of the conjugate IRDye800CW-Aff04 on HER2 positive cell line SKBR3 vs HER2 negative cell line A431.

The resulting kinetic profiles showed a $K_d$ associated to the conjugate IRDye800CW-Aff04 of $22.4±3.0×10^{-8}$ M, demonstrating that the polypeptide Aff-04 of the invention retains a remarkable affinity for the target in HER2+ cell line SK-BR-3 even after the conjugation step. Conversely, the conjugate IRDye800CW-Aff04 did not show any binding on HER2-cell line (A431), as shown in FIG. 3.

Example 9: Competitive ELISA of Aff04 Polypeptide Versus Trastuzumab or Pertuzumab A competitive ELISA assay has been developed in order to investigate if the epitope of the HER2/Neu antigen recognized by Aff04 polypeptide was distinct from the epitope recognized by the humanized monoclonal antibodies trastuzumab and pertuzumab, actually used in therapeutic treatments of HER2-positive tumors.

The first experiment, aimed at evaluating the quality of the assay, was a competitive ELISA assay carried out between trastuzumab and trastuzumab-biotin. Briefly, a Medisorp transparent plastic plate (96 wells, Thermo Scientific), was coated (64 wells) with 2.5 μg/mL of HER2/Fc chimeric protein in TBS pH 7.4 (1 h, RT). The wells were blocked with 0.5% BSA in TBS (1 h, RT).

Then different concentrations of trastuzumab (1.6, 0.8, 0.4, 0.2, 0.1, 0.05, 0.025 and 0 μg/mL) were incubated together with 0.2 μg/mL of trastuzumab-biotin in each well in triplicate (1 h at RT) in TBS+0.1% Tween 20 (TBS-T). At the end of the incubation, the plate was washed three times with 250 μL of TBS-T and incubated with Streptavidin-HRP 1:10000 in TBS-T (1 h at RT). The plate was washed again 3 times with TBS-T and developed 5 min with TMB reagent (100 μL). The reaction was blocked with 50 μL of sulfuric acid 2 M and read at 450 nm.

Figure 4:
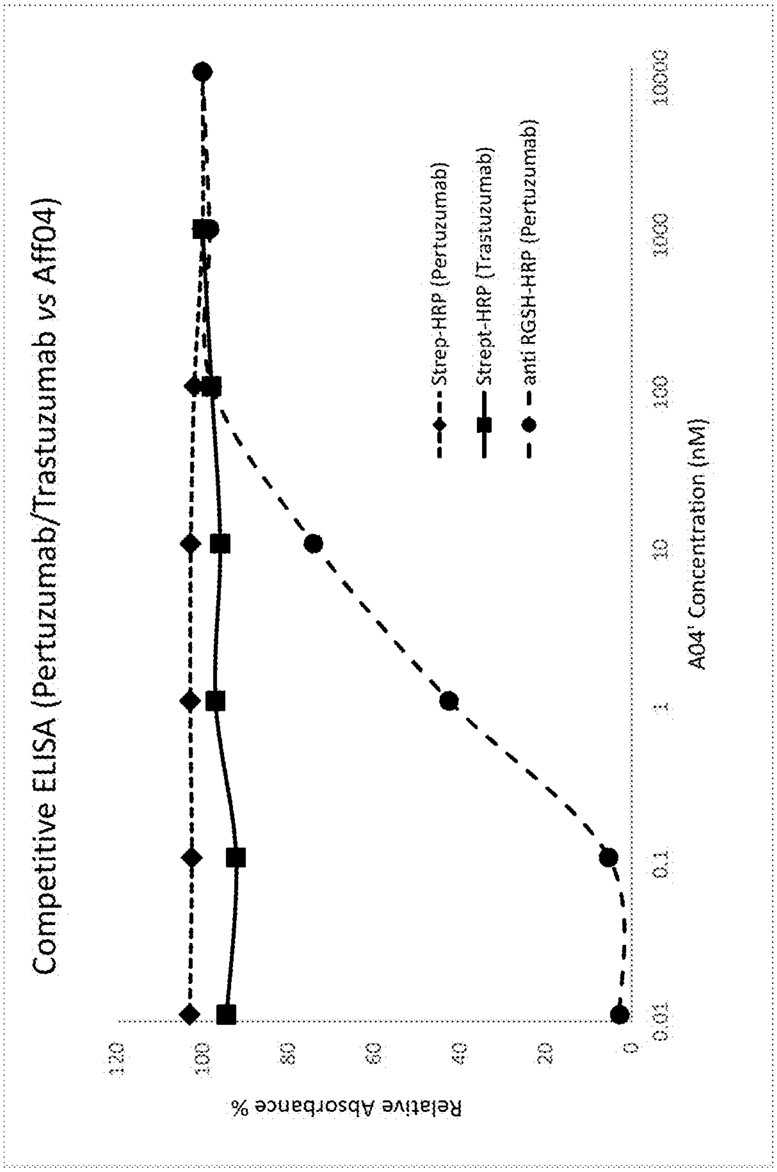
FIG. 4 reports the results of a competitive ELISA test with trastuzumab-biotin or pertuzumab-biotin vs Aff04 polypeptide.

The same experiment was then performed in three alternative assays with Aff04 vs trastuzumab-biotin or pertuzumab-biotin:

Assay a) Different concentrations of Aff04 (10000, 1000, 100, 10, 1, 0.1 and 0.01 ng/ml) were incubated together with 0.2 μg/mL of trastuzumab-biotin or pertuzumab-biotin in each well in triplicate. As positive control, the same experiment was repeated using an antibody anti RSGH TAG-HRP (1:4000) in place of streptavidin-HRP, in order to evaluate the curve affinity of Aff04 to HER2 receptor. The ELISA results, plotted in the diagram of FIG. 4, suggested that the trastuzumab-biotin, pertuzumab-biotin and Aff04 are all binders for HER2 receptor but the epitopes recognized by trastuzumab and pertuzumab are different from that recognized by Aff04 affitin.

Figure 5:
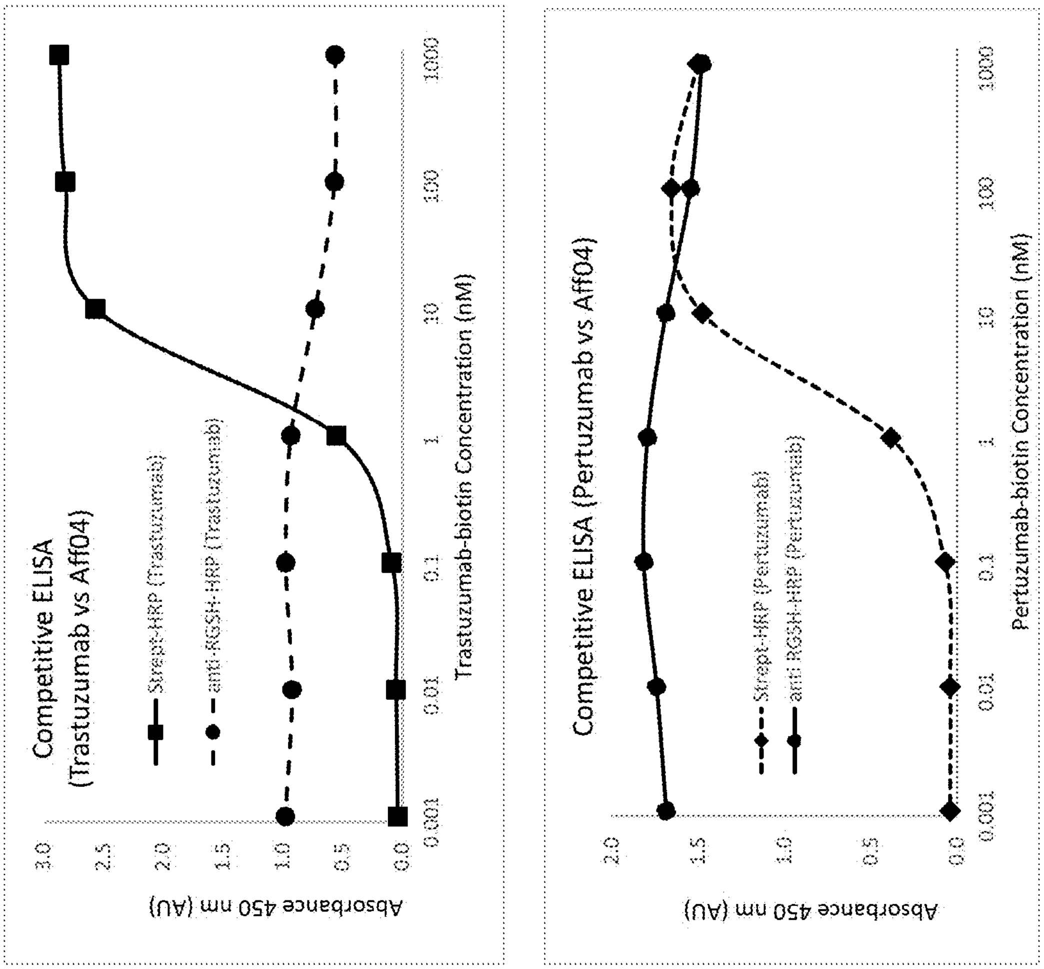
FIG. 5 reports the results of a different competitive ELISA test with trastuzumab-biotin vs Aff04 polypeptide (a) or pertuzumab-biotin vs Aff04 polypeptide (b)

Assay b) Additional competitive ELISA experiment was performed using a variable trastuzumab-biotin and pertuzumab-biotin concentrations in the presence of fixed Aff04 concentration. Briefly, a Medisorp transparent plastic plate (96 wells, Thermo Scientific) was coated (64 wells) with 2.5 μg/mL of Her2/Fc chimeric protein in TBS pH 7.4 (1 h, RT). The wells was blocked with 0.5% BSA in TBS (1 h, RT). Then different concentrations of trastuzumab-biotin (20000, 2000, 200, 20, 2, 0.2, 0.02 and 0 ng/mL) were incubated together with 10 μg/mL of Aff04 in each well in duplicate (1 h at RT) in TBS+0.1% Tween 20 (TBS-T). At the end of the incubation, the plate was washed three times with 300 μL of TBS-T and incubated with Streptavidin-HRP 1:10000 or anti-RSGH TAG-HRP 1:4000 in TBS-T (1 h at RT). The plate was washed again 3 times with TBS-T and developed 5 min with TMB reagent (100 μL). The reaction was blocked with 50 μL of sulfuric acid 2 M and read at 450 nm. From the ELISA results it is clear that the curves of Aff04 detected with anti RSGH-Tag Ab have a negligible response decrease when the trastuzumab-biotin or pertuzumab-biotin were increased (see FIGS. 5*a* and 5*b* respectively).

Assay c) Another competitive ELISA assay was performed in the same conditions using a variable concentration of trastuzumab-biotin and pertuzumab-biotin against buffer (no competition) and Aff04 (competition) in the same experimental condition of last competitive ELISA.

Figure 6:
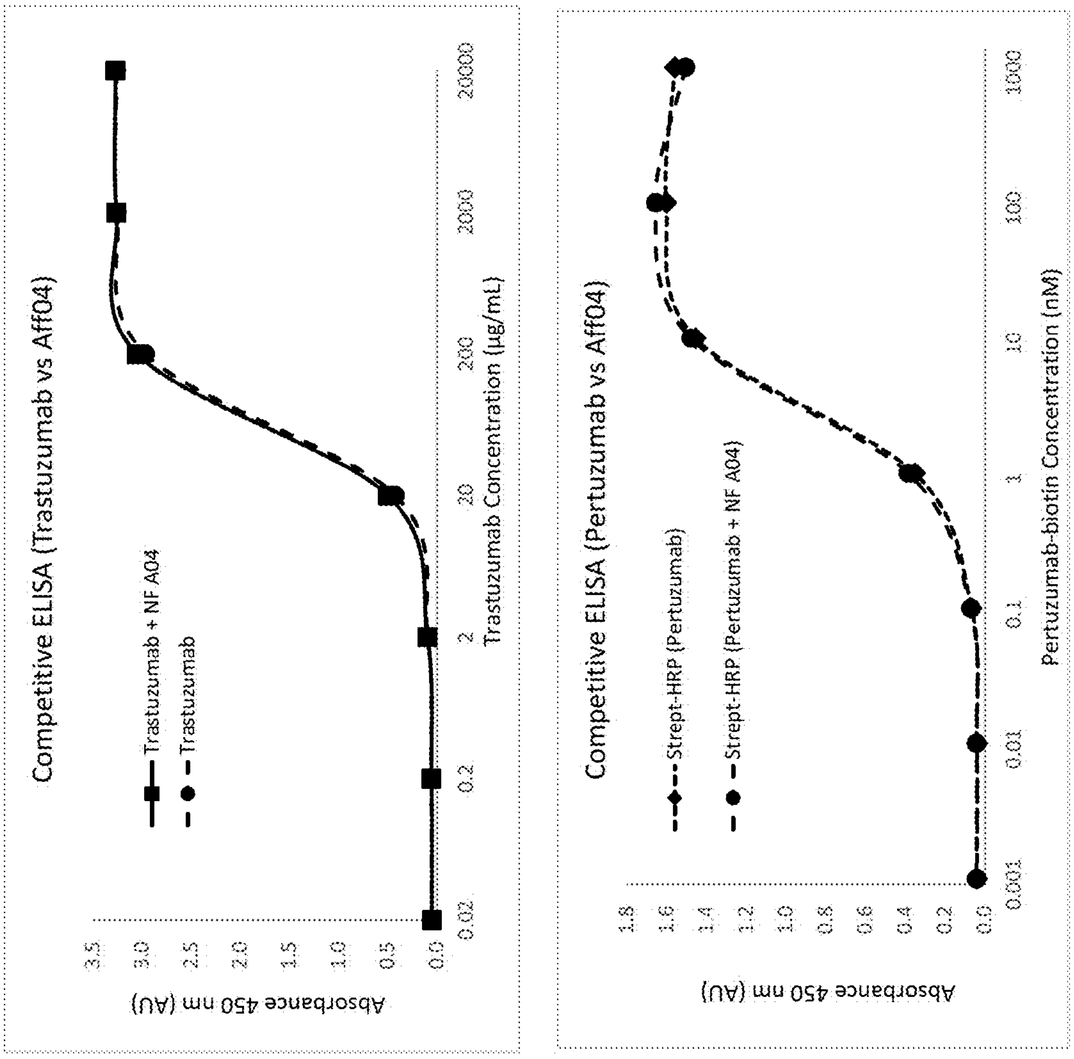
FIG. 6 reports the curves of trastuzumab (a) or pertuzumab (b) in the presence or absence of Aff04.

Overall, the results showed no competition between the targeted molecules, as the curves of both trastuzumab and pertuzumab were equal in the presence or absence of Aff04 affitin (see FIGS. 6*a* and 6*b* respectively).

It is clear from the diagrams that Aff04 retained the binding properties to HER2 and that its specificity for the receptor was not affected by the presence of the two reference antibodies. In fact, the competition studies demonstrated that the epitope recognized by the Aff04 is separate and distinct from the epitopes recognized by trastuzumab and pertuzumab monoclonal antibodies, so they do not compete for binding to HER2.

Example 10: In Vivo Biodistribution of Conjugate IRDye800CW-Aff04

In vivo optical imaging biodistribution of IRDye800CW-Aff04 was evaluated in healthy mice. Optical Imaging experiments on three healthy mice were performed using an IVIS Spectrum system after administration of IRDye800CW-Aff04 at a dose of 10 nmol/mouse, in an administration volume of 0.2 mL. The experiments were carried out at 15 min, 30 min, 1 h, 2 h, 4 h, 6 h, 24 h and 48 hours after intravenous administration of the conjugate.

Figure 7:
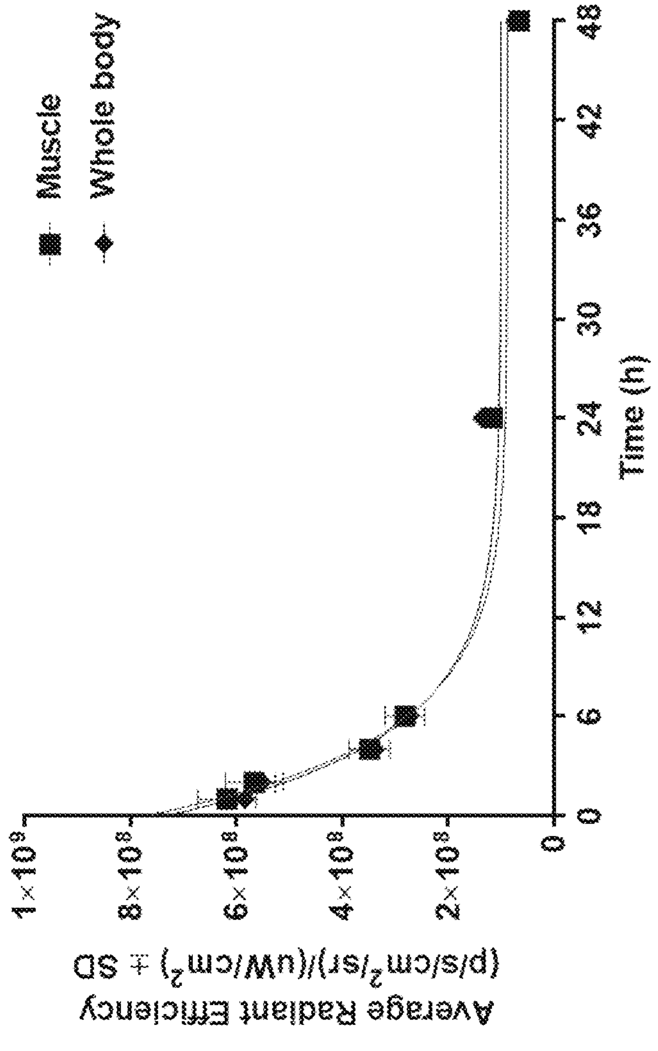
FIG. 7 reports the fluorescence signal curves of conjugate IRDye800CW-Aff04 administered at a dosage of 10 nmol/mouse in Balb/c nu/nu mice (Mean, St. Dev, n=3)

Regions of interest (ROIs) were drawn on a reference background healthy region (hind leg's muscle) of the mouse and on whole body for each fluorescence image at every time point to evaluate signal intensity in the tissues, expressed as Average Radiant Efficiency (see FIG. 7, reporting the fluorescence signal curves of IRDye800CW-Aff04 administered 10 nmol/mouse in Balb/c nu/nu mice).

Pharmacokinetic analysis of the signal was performed to evaluate the half time of the tested product by using a mono-exponential decay model and the results are reported in Table 3:

TABLE 3

Half life values for IRDye800CW-Aff04 in muscle and in the whole body

| | Muscle | Whole body |
|---|---|---|
| Half life (h) | 3.255 | 3.220 |

The two computed half-life values thus obtained were consistent, giving an average value of 3.23h.

Such values of biological half-life make the Aff04 conjugate potentially suitable as alternative tool for use in fast imaging protocols, for instance in optical imaging.

After sacrifice, several organs were collected for the measure of residual fluorescence (after 48h). The measurements of fluorescence signal intensity have been obtained from the analysis of each organ selecting an area of interest (ROIs) at the center of each sample. The analyzed organs were: kidney, lung, spleen, liver, muscle and heart.

Figure 8:
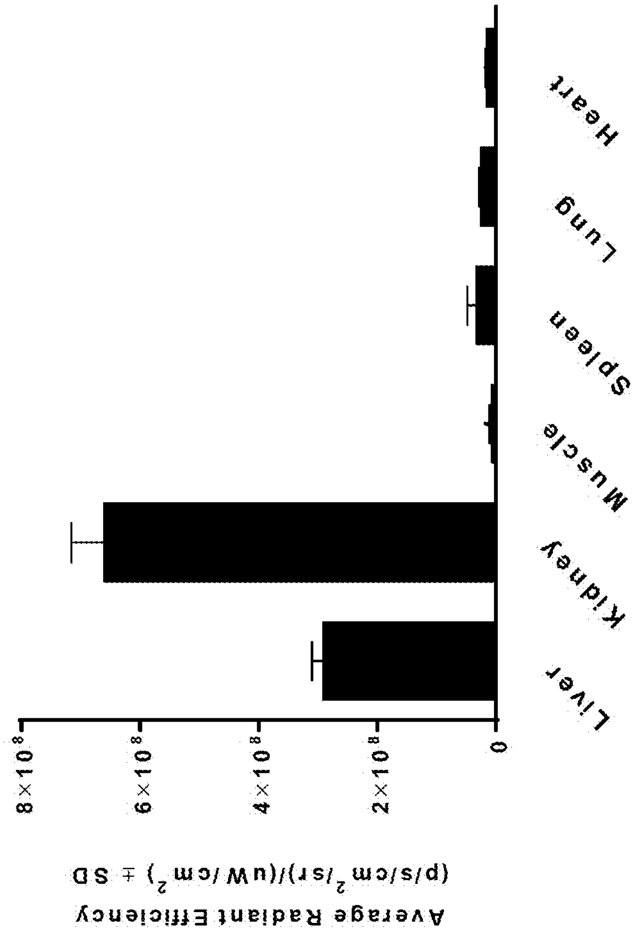
FIG. 8 reports the ex-vivo biodistribution of conjugate IRDye800CW-Aff04 in healthy mice at 48 h after injection at a dosage 10 nmol/mouse.

FIG. 8 shows the ex-vivo biodistribution of IRDye800CW-Aff04 in healthy mice at 48 h after injection at a dosage 10 nmol/mouse. The higher uptake of IRDye800CW-Aff04 in the kidneys shows that it is preferably cleared by the renal pathway instead of the hepatobiliary pathway.

REFERENCES

1. Slamon D. J. et al., Science 1989, 244, 707-712
2. McAfee J. G. et al, Biochemistry 1995, 34, 10063-10077
3. Mouratou B. et al, PNAS 2007, 104 (46), 17983-17988
4. Goux M. et al., Bioconjugated Chem. 2017, 28, 2361-2371
5. WO2009/080810 A1
6. Orlova A. et al., Cancer Res. 2006, 66 (8), 4339-4348
7. WO2012/096760 A1
8. WO2017/161096 A1
9. Bornhorst J. A. et al, Methods Enzymol. 2000, 326, 245-254
10. Huet S. et al, PLoS ONE 2015, 10 (11): e0142304

The invention claimed is:

1. A polypeptide that specifically binds to Human Epidermal Growth Factor Receptor 2 (HER2), comprising the amino acid sequence of SEQ ID NO: 1.

2. The polypeptide according to claim 1, consisting of the amino acid sequence of SEQ ID NO: 1.

3. The polypeptide according to claim 1, comprising the amino acid sequence of SEQ ID NO: 2.

4. The polypeptide according to claim 3, consisting of the amino acid sequence of SEQ ID NO: 2.

5. The polypeptide according to claim 1, which is linked to an imaging agent.

6. The polypeptide according to claim 5, wherein the imaging agent is selected from the group consisting of a fluorophore moiety, a magnetic or paramagnetic moiety, a radiolabeling isotope, an affinity label, an X-ray responsive moiety, an ultrasound responsive moiety, and a photoacoustic responsive imaging moiety.

7. The polypeptide according to claim 6, wherein the fluorophore moiety is a cyanine dye.

8. The polypeptide according to claim 6, wherein the radiolabeling isotope is selected from $^{18}F$, $^{124}I$, $^{11}C$, $^{64}Cu$, $^{68}Ga$, $^{89}Zr$, $^{44}Sc$, $^{99m}Tc$, indium, gallium, yttrium, bismuth, radioactinides and radiolanthanides.

9. The polypeptide according to claim 6, wherein the affinity label is biotin.

10. A diagnostic or imaging composition comprising the polypeptide as defined in claim 5 with pharmaceutically acceptable carriers, excipients, diluents and/or additives.

11. A method of imaging comprising:

administering the composition according to claim 10 to a subject; and imaging the subject with a diagnostic device.

12. The method according to claim 11, wherein said imaging is performed using an imaging technique selected from magnetic resonance, positron-emission tomography (PET), computed tomography (CT), ultrasounds (US), photoacoustic imaging (PAI), near-infrared fluorescence imaging (NIRF) and single photon emission computed tomography (SPECT).

13. A conjugate comprising a polypeptide consisting of the amino acid sequence of SEQ ID NO: 1, wherein the polypeptide is linked to an imaging agent.

14. The conjugate according to claim 13, wherein the imaging agent is selected from the group consisting of a fluorophore moiety, a magnetic or paramagnetic moiety, a radiolabeling isotope, an affinity label, an X-ray responsive moiety, an ultrasound responsive moiety, and a photoacoustic responsive imaging moiety.

15. The conjugate according to claim 14, wherein the fluorophore moiety is a cyanine dye.

16. The conjugate according to claim 14, wherein the radiolabeling isotope is selected from $^{18}F$, $^{124}I$, $^{11}C$, $^{64}Cu$, $^{68}Ga$, $^{89}Zr$, $^{44}Sc$, $^{99m}Tc$, indium, gallium, yttrium, bismuth, radioactinides and radiolanthanides.

17. The conjugate according to claim 14, wherein the affinity label is biotin.

18. A diagnostic or imaging composition comprising the conjugate as defined in claim 13 with pharmaceutically acceptable carriers, excipients, diluents and/or additives.

19. A method of imaging comprising:

administering the composition according to claim 18 to a subject; and imaging the subject with a diagnostic device.

20. The method according to claim 19, wherein said imaging is performed using an imaging technique selected from magnetic resonance, positron-emission tomography (PET), computed tomography (CT), ultrasounds (US), photoacoustic imaging (PAI), near-infrared fluorescence imaging (NIRF) and single photon emission computed tomography (SPECT).

* * * * *